United States Patent
Alouini et al.

(10) Patent No.: US 9,835,546 B2
(45) Date of Patent: Dec. 5, 2017

(54) SYSTEM AND METHOD OF ANALYSIS BY DETERMINING A DEPOLARIZING OR DICHROIC CHARACTER OF AN OBJECT

(75) Inventors: Mehdi Alouini, Gosne (FR); Julien Fade, Rennes (FR)

(73) Assignee: UNIVERSITE DE RENNES 1, Rennes (FR)

( * ) Notice: Subject to any disclaimer, the term of this patent is extended or adjusted under 35 U.S.C. 154(b) by 134 days.

(21) Appl. No.: 14/128,793

(22) PCT Filed: Jun. 18, 2012

(86) PCT No.: PCT/EP2012/061585
§ 371 (c)(1),
(2), (4) Date: Mar. 28, 2014

(87) PCT Pub. No.: WO2012/175451
PCT Pub. Date: Dec. 27, 2012

(65) Prior Publication Data
US 2014/0285803 A1    Sep. 25, 2014

(30) Foreign Application Priority Data
Jun. 23, 2011   (FR) ..................... 11 55527

(51) Int. Cl.
*G01N 21/21*   (2006.01)
*G01N 21/19*   (2006.01)

(52) U.S. Cl.
CPC .......... *G01N 21/21* (2013.01); *G01N 21/19* (2013.01); *G01N 2021/217* (2013.01)

(58) Field of Classification Search
CPC ........ G01J 4/00; G01J 4/02; G01J 4/04; G01J 2004/001; G01J 2004/002;
(Continued)

(56) References Cited

U.S. PATENT DOCUMENTS 3,446,557 A  *  5/1969  Wilkinson  .............  G01N 21/19
250/225
3,450,478 A  *  6/1969  Sebestyen  .............  G01N 21/19
250/225
(Continued)

FOREIGN PATENT DOCUMENTS

WO    WO 2010/081999 A1 *  7/2010

OTHER PUBLICATIONS

"Optical Activity and Circular Dichroism," 2003, https://www.rose-hulman.edu/~brandt/Chem430/Cd.pdf, pp. 1-8.*
(Continued)

*Primary Examiner* — Gordon J Stock, Jr.
(74) *Attorney, Agent, or Firm* — Nixon & Vanderhye, PC (57) ABSTRACT

An analysis system comprises a transmitting device (1.1) and a receiving device (1.2). The transmitting devices comprises means for illuminating an object (1.3), or a part of the object, by a first light beam (1.8) consisting of signals with two distinct frequencies and first orthogonal polarisation states. The receiving device comprises means (1.6) for detecting, in a second light beam with second polarisation states and resulting from the illumination of the object to be analysed by the first light beam, a signal at a beat frequency equal to a difference between the two frequencies of the first light beam; and means (1.7) for obtaining information relating to the depolarising or dichroic character of the object, or of the part of the object, according to the detection or not of a signal at the beat frequency.

5 Claims, 3 Drawing Sheets (58) Field of Classification Search
CPC ........... G01J 2004/004; G01J 2004/005; G01J 2004/007; G01J 2004/008; G01N 21/19; G01N 21/21; G01N 21/216; G01N 21/217; G01N 21/218; G01N 21/23; G01N 2021/217; G01M 11/30; G01M 11/31; G01M 11/3109; G01M 11/3118; G01M 11/3127; G01M 11/3136; G01M 11/3145; G01M 11/3154; G01M 11/3163; G01M 11/3172; G01M 11/3181; G01M 11/33; G01M 11/331; G01M 11/332; G01M 11/333; G01M 11/334; G01M 11/335; G01M 11/336; G01M 11/337; G01M 11/338
USPC ......................... 356/73.1, 128–137, 364–370
See application file for complete search history.

(56) References Cited

U.S. PATENT DOCUMENTS

| | | | | |
|---|---|---|---|---|
| 3,741,660 A | * | 6/1973 | Abu-Shumays | G01N 21/19 250/225 |
| 3,926,524 A | * | 12/1975 | Margulies | G01N 21/19 356/327 |
| 4,449,825 A | * | 5/1984 | May | G01N 21/23 356/484 |
| 5,227,715 A | * | 7/1993 | Ito | G01R 15/247 250/225 |
| 5,291,266 A | * | 3/1994 | Burns | G02B 27/283 356/477 |
| 6,157,448 A | * | 12/2000 | Kowa | G01N 21/23 356/365 |
| 6,327,037 B1 | | 12/2001 | Chou et al. | |
| 2003/0081221 A1 | | 5/2003 | Sanzari | |
| 2009/0213374 A1 | * | 8/2009 | Otani | G01N 21/23 356/364 |

OTHER PUBLICATIONS

Schellman, John, "Circular Dichroism and Optical Rotation," 1975, Chemical Reviews, vol. 75, No. 3, pp. 323-331.*

English-language translation of the Written Opinion of the International Searching Authority for PCT/EP2012/061585, dated Jul. 23, 2012.

International Search Report for PCT/EP2012/061585, dated Jul. 23, 2012.

* cited by examiner

SYSTEM AND METHOD OF ANALYSIS BY DETERMINING A DEPOLARIZING OR DICHROIC CHARACTER OF AN OBJECT

This application is the U.S. national phase of International Application No. PCT/EP2012/061585, filed 18 Jun. 2012, which designated the U.S. and claims priority to FR Application No. 11/55527, filed 23 Jun. 2011.

BACKGROUND OF THE INVENTION (1) Field of the Invention

The present invention concerns a system and a method of analysis of an object, or of a sample, by determining its depolarising or dichroic character.

It is considered that an object has a dichroic character if it exhibits loss anisotropy.

Polarimetric imaging finds applications in a large number of fields, and in particular in the field of biomedical imaging. Polarimetric imaging is based on an analysis of the modification of the state of polarisation of a light beam when it is back-scattered or forward-scattered by an object, or a sample, to be analysed.

In dermatology for example, polarimetric images of the skin may allow detecting melanomas or lupus. Polarimetric imaging also allows detecting irradiation of the skin, much before the clinical signs of such irradiation appear. Another application is support to the diagnosis of pathologies on biological tissues for detecting cancer of the uterus or for analysing liver cirrhosis progress.

(2) Description of Related Art

All these techniques are based on perfect knowledge of the polarimetric state of the light beam projected onto the object or sample to be analysed and on a precise measurement of the state of polarisation of the light beam forward-scattered or back-scattered by the object or sample to be analysed. Such an approach is not very compatible with the use of an optical guide, such as an optical fibre, for transferring the effective transmission and/or effective reception of the light beam. This constraint considerably limits the fields of application of polarimetric imaging, in particular with regard to in situ and/or in vivo medical diagnoses.

This is because an optical fibre always exhibits residual birefringencies that change in particular according to the curvatures of the fibre, which is for example the case in endoscopic imaging, where the fibre undergoes mechanical compression and torsion stresses that are in principle unpredictable. These residual birefringencies cause variations that are not deterministic of the polarimetric state of the light beam during propagation thereof in the optical fibre.

So as to allow transfer by optical fibre, the patent application published under the reference FR 2 941 047 A1 proposes a mechanism for determining information on polarisation of a measurement point of a sample by using means for rotating the polarisation disposed at the end of the optical fibre on the same side as the sample to be analysed. The birefringent or depolarising character of the sample, at a given point, is then obtained by statistical analysis of shots of various random polarisation states at the entry to the fibre. However this proposition requires an acquisition time for the measurements that is incompatible with the real-time imaging and endoscopic imaging requirements.

BRIEF SUMMARY OF THE INVENTION

It is desirable to overcome these various drawbacks of the prior art.

It is in particular desirable to provide a solution that enables performing analyses on an object by determining all or part of the depolarising or dichroic character of all or part of this object, whether it be in free space or by transfer by means of an optical guide such as an optical fibre.

It is in particular desirable to provide a solution that enables performing such analyses quickly.

It is in particular desirable to provide a solution that is applicable to biomedical analyses and more particularly to biomedical imaging.

It is in particular desirable to provide a solution that is applicable to analyses in environments that are hostile and/or difficult of access.

It is in particular desirable to provide a solution that is applicable to analyses of surface states and to classifying materials.

It is in particular desirable to provide a solution that is simple to implement and at low cost.

The invention concerns a system of analysis by determining a depolarising or dichroic character of all or part of an object to be analysed, said system comprising a transmitting device and a receiving device. The system is such that the transmitting device comprises means for illuminating the object to be analysed, or part of the object to be analysed, by a first light beam consisting of two distinct optical frequencies and with first orthogonal polarisation states. The system is also such that the receiving device comprises: means for detecting, in a second light beam with second polarisation states and resulting from the illumination of the object to be analysed by said first light beam, a signal at a beat frequency equal to a difference between the two optical frequencies constituting said first light beam; means for obtaining information relating to the depolarising or dichroic character of the object to be analysed, or of said part of the object to be analysed, according to the detection or not of a signal at the beat frequency.

Thus, by simply performing a verification of the preservation or not of the orthogonality of the polarisation states by detecting the signal at the beat frequency, the states of polarisation of the light beam resulting from the illumination of the object to be analysed or of the part of the object to be analysed are not analysed as such. The analyses carried out simply on the basis of a verification of the preservation or not of the orthogonality of the polarisation states are thus more rapid, simpler to implement and at less cost, since they do not require means for analysing polarisation on reception. In addition, since the orthogonality of the polarisation states is not sensitive to the residual birefringencies of the optical guides, such as the optical fibres, the analyses carried out gain in flexibility through the possibility of use of such optical guides.

According to a particular embodiment, the means for obtaining the information relating to the depolarising or dichroic character of the object to be analysed, or of said part of the object to be analysed, comprise means for determining the amplitude of the signal at the beat frequency.

Thus it is possible to base the analysis on a quantification of the depolarising or dichroic character of the object to be analysed, or of the part of the object to be analysed.

According to a particular embodiment, the transmitting device is adapted so that the means for illuminating the object to be analysed, or said part of the object to be analysed, perform the illumination via a first optical guide.

Thus it is possible to perform the measurement in an environment, in which the object to be characterised is situated, that is difficult of access.

According to a particular embodiment, the receiving device comprises means for capturing light and for converting a captured light signal into an electrical signal, said means having a bandwidth defined according to the beat frequency.

According to a particular embodiment, the receiving device comprises means for receiving via a second optical guide the light beam resulting from the illumination of the object to be analysed by said first light beam.

Thus it is possible to perform the measurement in an environment, in which the object to be characterised is situated, that is difficult of access.

According to a particular embodiment, the second optical guide is placed upstream of the means for capturing light and for converting a captured light into an electrical signal.

According to a particular embodiment, the analysis system comprises means for generating a complete or partial image of the object to be analysed from information relating to the depolarising or dichroic character of several parts of the object to be analysed.

Thus it is possible to perform biomedical analyses in a simple and rapid manner and at low cost, particularly in the field of biomedical imaging.

According to a particular embodiment, the analysis system comprises means for determining values of mechanical or temperature stresses applied to the object to be analysed, from information relating to the dichroic character of the object to be analysed.

Thus it is possible to perform analyses of mechanical or temperature stresses related to an environment that is potentially hostile and/or difficult of access, and this in a simple and rapid manner and at low cost.

According to a particular embodiment, the analysis system comprises means for modifying the optical frequencies constituting said first light beam so that they preserve the same difference and means for classifying the object to be analysed, or said part of the object to be analysed, according to information relating to the depolarising or dichroic character of the object to be analysed, or of said object part to be analysed, obtained for various respective pairs of frequencies constituting said first light beam.

Thus it is possible to effect spectro-polarimetric analyses and to perform analyses of surface states or of classification of materials, and this in a simple and graphic manner and at low cost, since the measurement does not require means for analysing the polarisation.

The invention also concerns a method of analysis by determining a depolarising or dichroic character of all or part of an object to be analysed, said method being implemented by an analysis system comprising a transmitting device and a receiving device. The method is such that the transmitting device performs a step of illuminating the object to be analysed, or a part of the object to be analysed, by a first light beam consisting of two distinct optical frequencies and with first orthogonal polarisation states. The method is further such that the receiving device performs steps of: detecting, in a second light beam with second polarisation states and resulting from the illumination of the object to be analysed by said first light beam, a signal at a beat frequency equal to a difference between the two optical frequencies constituting said first light beam; obtaining information relating to the depolarising or dichroic character of the object to be analysed, or of said part of the object to be analysed, according to the detection or not of a signal at the beat frequency.

BRIEF DESCRIPTION OF THE SEVERAL VIEWS OF THE DRAWINGS

The features of the invention mentioned above, as well as others, will emerge more clearly from a reading of the following description of an example embodiment, said description being given in relation to the accompanying drawings, among which.

DETAILED DESCRIPTION OF THE INVENTION

So as to determine the depolarising or dichroic character of an object, whether it be in free space or by transfer by means of an optical guide such as an optical fibre, it is proposed that the object to be analysed be illuminated by a light beam consisting of two distinct optical frequencies with orthogonal polarisation states. The polarisation states are said to be orthogonal in the mathematical sense of the term and thus two right and left circular polarisations are orthogonal. It is then sought whether a signal is present at a beat frequency in the light beam resulting from the illumination of the object to be analysed, i.e. from the forward-scattering or back-scattering by the object to be analysed of the first light beam consisting of signals at two distinct optical frequencies and with orthogonal polarisation states. If a signal is present at this beat frequency, this means that orthogonality between the polarisation states of the forward-scattered or back-scattered signals is no longer kept and that the object has a depolarising or dichroic character; otherwise this means that orthogonality between the polarisation states of the forward-scattered or back-scattered signals is kept and that the object does not exhibit any depolarising or dichroic character. It should be noted that it is solely sought to check whether orthogonality of the polarisation states is kept, and not to analyse the polarisation states as such. It should be noted that, accordingly, this principle does not require any use of components for polarimetric analysis on reception. It should be noted that this principle is also applicable to only part of the object.

Optical fibre can be used for transferring, with respect to the position of the object to be analysed, the generation of light beams serving to illuminate the object to be analysed and/or for transferring, with respect to the position of the object to be analysed, the analysis of the light beam resulting from the illumination of the object to be analysed. This is because the residual birefringencies of the optical fibre may imply a phase shift of the polarisation axes and/or a rotation of the polarisation states, but do not affect the orthogonality of the polarisation states. The orthogonality of polarisation states is then preserved during the transport of the light beam by optical fibre. Likewise the non-orthogonality of the polarisation states is preserved during the transport of the light beam by optical fibre.

Thus it is detected whether a signal is present at the beat frequency either directly in the light beam resulting from the illumination of the object to be characterised, or in the light beam resulting from the transport via the optical guide of the light beam resulting from the illumination of the object to be characterised.

Thus the analysis system uses a measurement phase and a measurement use phase, and the use of any measurement takes place on the basis of the compliance or not with the orthogonality of the polarisation states, i.e. on the analysis of a signal at the beat frequency, rather than on the polarisation states themselves.

Figure 1:
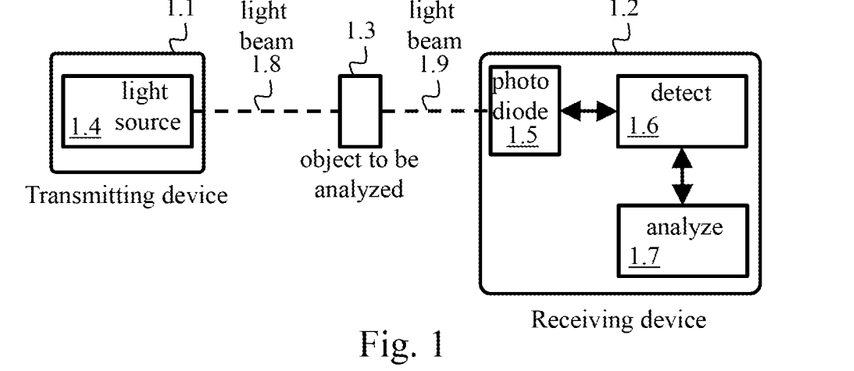
FIG. 1 schematically illustrates a first embodiment of a system of analysis by determining the depolarising or dichroic character of all or part of an object.

FIG. 1 schematically illustrates a first embodiment of a system of analysis by determining a depolarising or dichroic character of all or part of an object.

The system comprises a transmitting device 1.1 and a receiving device 1.2. An object to be analysed 1.3 is placed between the transmitting device 1.1 and the receiving device 1.2, meaning a light beam 1.8 generated by the transmitting device 1.1 for illuminating the object 1.3 implies a light beam 1.9 transmitted by the object to be analysed 1.3. This thus means that the object to be analysed 1.3 is placed between the transmitting device 1.1 and receiving device 1.2, even when the light beam 1.9 results from the back-scatter of the light beam 1.8. In other words, the transmitting device 1.8 is adapted to illuminate the object to be analysed 1.3 and the receiving device 1.2 is adapted to receive the light beam 1.9 forward-scattered or back-scattered by the object to be analysed 1.3 following the illumination by the transmitting device 1.1.

The transmitting device 1.1 may be adapted to illuminate only part of the object to be analysed 1.3 and the receiving device 1.2 adapted to receive the light beam forward-scattered or back-scattered by this part of the object to be analysed 1.3.

The term object must be interpreted in the broad meaning, since this may be an inert body, a living-body sample, etc.

The transmitting device 1.1 comprises a light source 1.4 that generates the light beam 1.8 serving to illuminate the object to be analysed 1.3. The light source 1.4 is adapted to generate a light beam consisting of signals with two distinct optical frequencies $v_1$ and $v_2$ and with orthogonal polarisation states. As a reminder, the polarisation states are said to be orthogonal in the mathematical sense of the term and they are not necessarily linear.

The light source 1.4 may comprise two monomode lasers, one generating the signal at the frequency $v_1$ and the other generating the signal at the frequency $v_2$, and combined so as to exhibit two orthogonal polarisations.

In a variant embodiment, the light source 1.4 comprises a bifrequency laser oscillating simultaneously on two modes, according to two orthogonal polarisations, one having a natural frequency corresponding to $v_1$ and the other having a natural frequency corresponding to $v_2$.

According to another variant embodiment, the light source 1.4 consists of a monofrequency laser, division means, a frequency translator and recombination means. The wave generated by the monofrequency laser at the frequency $v_1$ is divided into two channels by the division means. One of the two channels is offset by a frequency $\Delta v$ by the frequency translator, and then the two channels are recombined by the recombination means with orthogonal polarisation states.

The receiving device 1.2 is adapted to receive the light beam 1.9 corning from the object to be analysed 1.3, following the illumination thereof by the light beam 1.8. The light beam 1.9 has polarisation states resulting from the incidence of the object to be analysed 1.3 on the light beam 1.8.

The receiving device 1.2 preferentially comprises a photodiode 1.5, the bandwidth of which is adapted to measure an optical signal at a frequency $\Delta v$, referred to as beat frequency, predefined according to the frequencies $v_1$ and $v_2$.

The beat frequency is fixed as being the difference between the frequencies $v_1$ and $v_2$. Thus:

$$\Delta v = v_1 - v_2$$

The photodiode 1.5 may be replaced by any device producing an electrical signal from an optical signal and insensitive to the polarisation of light. It is possible to use a photoconductor, a bolometer, a quantum cascade detector, etc. More generally, such a system has means for capturing light and for converting a captured light signal into an electrical signal.

The photodiode 1.5 may be preceded by an optical amplifier or followed by an electrical amplifier or a transimpedance amplifier, the signal amplification characteristics of which are predefined.

The receiving device 1.2 also comprises means 1.6 for detecting, in the light beam 1.9, a signal at the beat frequency $\Delta v$.

The receiving device 1.2 also comprises analysis means 1.7 adapted to determine the depolarising or dichroic character of the object to be analysed 1.3, according to the detection or not of a signal at the beat frequency $\Delta v$.

If the object to be analysed 1.3 is not depolarising, or does not exhibit any dichroic character, the light beam 1.9 preserves the orthogonal character of the polarisation states at the frequencies $v_1$ and $v_2$. Consequently the photodiode 1.5 produces a continuous electrical signal. This behaviour remains valid even if the object to be analysed 1.3 introduces a birefringence and/or a rotation of the polarisation states.

Conversely, if the object to be analysed 1.3 is depolarising, or if it presents an absorption anisotropy, i.e. has a dichroic character, then a part of the field of frequency $v_1$ associated with the first polarisation state is projected onto the second polarisation state of frequency $v_2$, and vice versa. The same applies if only part of the object to be analysed 1.3 is considered. The result is a modulation of the intensity of the signal at the beat frequency $\Delta v$. In other words, if a signal is present in the light beam 1.9 at the beat frequency $\Delta v$, the electrical signal produced by the photodiode 1.5 exhibits an oscillation at this same frequency $\Delta v$.

Thus, if the electrical signal produced by the photodiode 1.5 is continuous, this means that the object to be analysed 1.3, or the part of the object to be analysed 1.3, does not exhibit any depolarising or dichroic character; and if the electrical signal produced by the photodiode 1.5 is not continuous, this means that the object to be analysed 1.3, or the part of the object to be analysed 1.3, exhibits a depolarising or dichroic character.

In addition, the amplitude of the signal modulated at the beat frequency $\Delta v$ is directly proportional to the depolarising or dichroic ability of the object to be analysed 1.3. It is thus possible to quantify the depolarising or dichroic character of the object to be analysed 1.3 according to the amplitude of the oscillations present on the electrical signal produced by the photodiode 1.5. This behaviour remains valid even if the object to be analysed 1.3 exhibits birefrigency and/or causes a rotation of the polarisation states.

Figure 3:
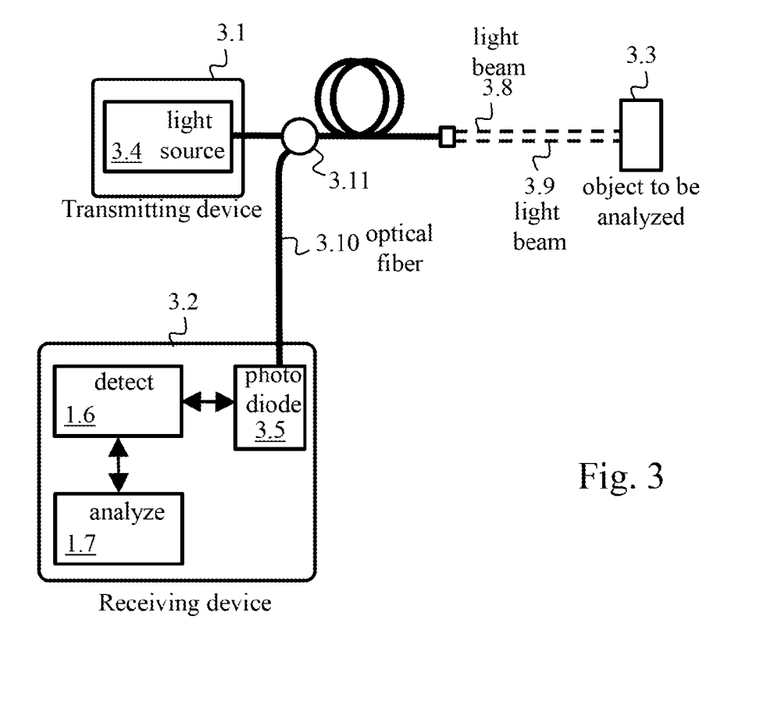
FIG. 3 schematically illustrates a second embodiment of a system of analysis by determining the depolarising or dichroic character of all or part of an object.
Figure 4:
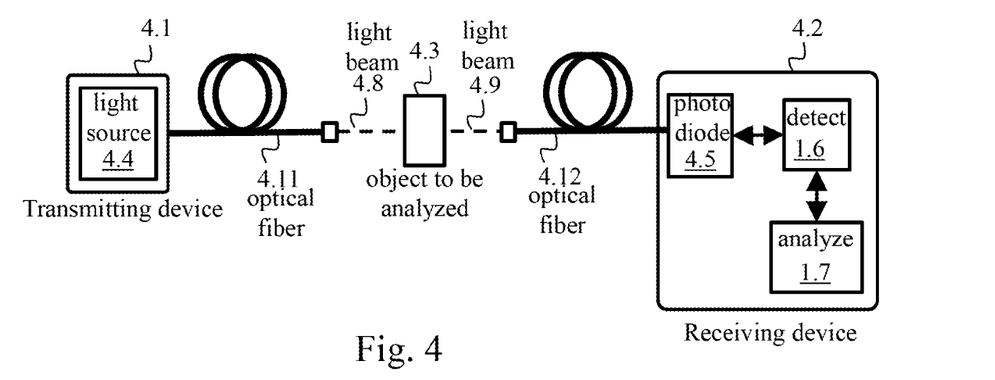
FIG. 4 schematically illustrates a third embodiment of a system of analysis by determining of the depolarising or dichroic character of all or part of an object.

It should be noted that the system presented in relation to FIG. 1, as well as those presented hereinafter in relation to FIGS. 3 and 4, does not have any polariser, polarising analyser or polarising cube receiving the light beam 1.9 upstream of the photodiode 1.5. This system determines the depolarising or dichroic character of the object to be analysed 1.3 simply by checking whether the orthogonality of the polarisation states of the signals at the frequencies $v_1$ and $v_2$ is preserved. This system does not perform any analysis of the polarisation states as such and thus does not seek to determine whether these polarisation states are linear, circular or elliptical, nor to verify whether the polarisation states of the signals of the light beam 1.8 generated by the light source 1.4 are preserved in the light beam 1.9. This system therefore enables a rapid analysis at reduced cost of the object to be analysed 1.3. In addition, since this system does not make any analysis of polarisation state as such, it allows transferring, with respect to the position of the object to be analysed 1.3, the generation of the light beam serving to illuminate the object to be analysed 1.3 and/or transferring, with respect to the position of the object to be analysed 1.3, the analysis of the light beam 1.9 resulting from the forward-scatter/back-scatter of the incident beam 1.8 by the object to be analysed 1.3. FIGS. 3 and 4 present such transfers by optical fibre.

Figure 5:
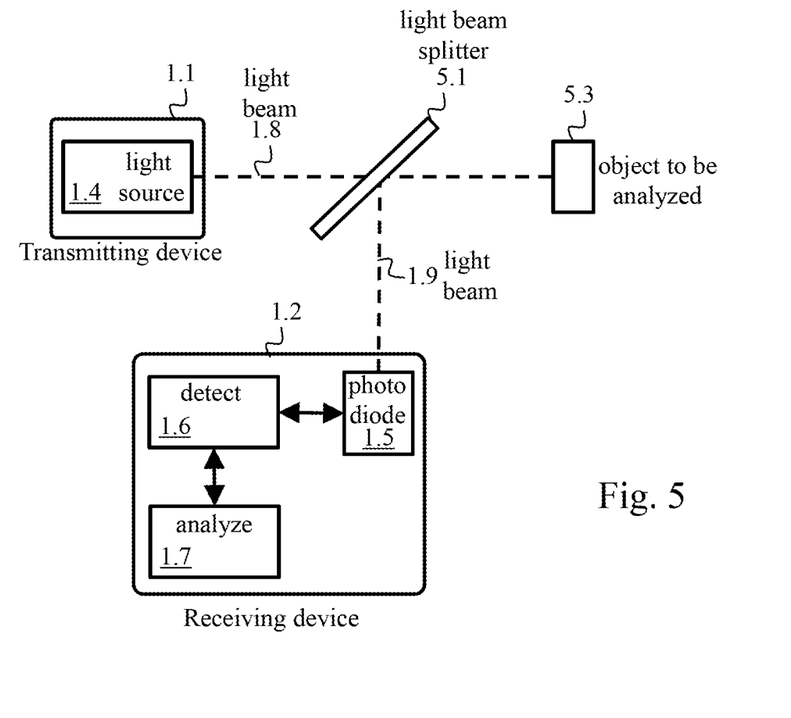
FIG. 5 schematically illustrates a fourth embodiment of a system of analysis by determination of the polarising or dichroic character of all or part of an object.

So that the receiving device 1.2 receives the light beam back-scattered by the object to be analysed 1.3, it is possible to use a light-separating device to direct this light beam to the receiving device 1.2. The light-separating device must not introduce any dichroism or depolarisation, so as not to have any effect on the analysis to be performed. A light-beam splitter 5.1 can be used for this purpose, as shown in FIG. 5, where the light beam 1.9 retro-reflected from an object to be analysed 1.3 is redirected to the receiving device 1.2 by the splitter 5.1. The splitter 5.1, although placed on the path of the light beam 1.8, has no effect thereon.

The analysis system, whether or not it uses a transfer by optical guide, and whether or not it uses a back-scattered light beam, is particularly suited to polarimetric imaging. In this case, the system comprises means for generating a complete or partial image of the object to be analysed from information relating to the depolarising or dichroic character of several parts of the object to be analysed. It is thus possible to perform a succession of measurements by moving the object to be analysed by means of a piezoelectric positioning plate, or any other precision device for moving the object to be analysed, the transmitting device 1.1 and the receiving device 1.2 being maintained in position.

Another possibility consists of using systems of beam pointing by galvanometric mirrors or any other means for successively controlling and directing the illumination beam in various parts of the object to be analysed, in order to scan the whole object or of the object part to be analysed. In the context of an illumination transferred by optical guide, it is possible to use a system for scanning the beam by galvanometric mirrors that would be placed at the end of the optical guide.

Thus the receiving device 1.2 obtains information relating to the depolarising or dichroic character of several parts of the object to be analysed, and an image of the object to be analysed is generated according to said information.

Apart from the biomedical diagnoses already mentioned, such a system enables distinguishing between metal material and insulating material, or to effect diagnoses of surface states.

In the context of polarimetric imaging, the photodiode 1.5 can then be replaced by a matrix of photodiodes, a CCD (Charge-Coupled device) sensor or a CMOS (Complementary Metal Oxide Semiconductor) sensor, and a bundle of optical fibres may be used to illuminate the object to be analysed.

The analysis system using a back-scattered light beam, whether or not it uses a transfer by optical guide, is particularly suited to spectro-polarimetric analysis. The system then comprises means for defining various values of the frequencies $v_1$ and $v_2$ so that they preserve the same difference $\Delta v$. The transmitting device then comprises means for modifying the frequencies $v_1$ and $v_2$ in order to apply these predefined values. It is thus possible to cover a broad spectral band without any modification of the beat frequency $\Delta v$. The receiving device 1.2 obtains information relating to the depolarising or dichroic character of the object to be analysed, or of a part of the object to be analysed, each of these items of information being associated with a pair of frequencies $v_1$ and $v_2$. The system then comprises means for classifying the object to be analysed, or part of the object to be analysed, in a predefined classification of materials, according to the obtained information.

Figure 2:
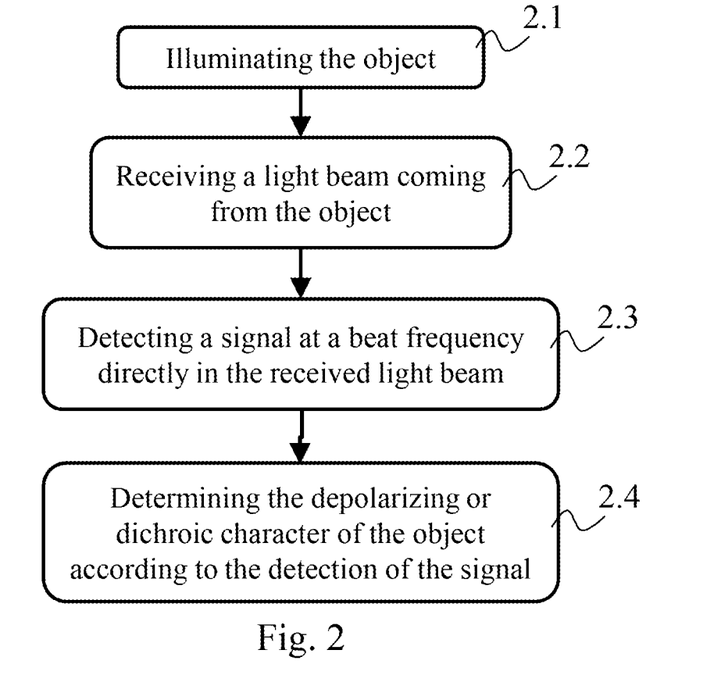
FIG. 2 schematically illustrates a method for determining the depolarising or dichroic character of all or part of an object.

FIG. 2 schematically illustrates a method for determining the depolarising or dichroic character of an object.

In a step 2.1, a transmitting device, such as the transmitting device 1.1, generates a light beam consisting of two distinct optical frequencies $v_1$ and $v_2$ with orthogonal polarisation states, and illuminates an object to be analysed, or a part of an object to be analysed, by means of this light beam. This light beam will be referred to as incident light beam.

In a following step 2.2, a receiving device, such as the receiving device 1.2, receives a light beam 1.9 coming from the object to be analysed, following the forward-scatter/back-scatter of the incident light beam 1.8 on the object to be analysed 1.3. This light will be referred to as resultant light beam.

In a following step 2.3, the receiving device detects a signal at a frequency $\Delta v$, referred to as beat frequency, predefined according to the frequencies $v_1$ and $v_2$. The receiving device detects whether a signal is present or not at this beat frequency $\Delta v$ and preferentially determines the amplitude of this signal if present.

In a following step 2.4, the receiving device determines the depolarising or dichroic character of the object to be analysed, or of the part of the object to be analysed, according to whether or not a signal at the beat frequency $\Delta v$ is detected. In other words, the receiving device obtains information relating to the depolarising or dichroic character of the object to be analysed or of the part of the object to be analysed.

The control of transmission and reception of the light beam, the detection of a signal at the beat frequency, the obtaining of the information relating to the depolarising or dichroic character and the subsequent analyses can be implemented in software form by the execution of a set of instructions by a programmable machine, such as DSP (Digital Signal Processor) or a processor, or be implemented in hardware form by a machine or a dedicated component, such as an FPGA (Field-Programmable Gate Array) or an ASIC (Application-Specific Integrated Circuit). In the context of implementation in software form, a processor executes instructions loaded into a Random Access Memory (RAM) from a Read-Only Memory (ROM), a storage medium or a communications network. These instructions form a computer program causing the implementation of at least one of the aforementioned steps.

FIG. 3 schematically illustrates a second embodiment of a system of analysis by determining the depolarising or dichroic character of an object 3.3.

Implementation of the system shown in FIG. 3 is similar to that of the system of FIG. 1, except that an optical fibre 3.10 is used to transfer, with respect to the position of the object to be analysed 3.3, the generation of the light beam serving to illuminate the object to be analysed 3.3 and to transfer, with respect to the position of the object to be analysed 3.3, the analysis of the light beam 3,9 resulting from the forward-scatter/back-scatter of the incident light beam 3.8 by the object to be analysed 3.3.

The system comprises transmitting 3.1 and receiving 3.2 devices.

The transmitting device 3.1 comprises a light source 3.4 adapted to generate a light beam consisting of signals with two distinct optical frequencies $v_1$ and $v_2$ and with orthogonal polarisation states. The light source 3.4 is also adapted to illuminate the object to be analysed 3.3 via the optical Fibre 3.10. The object to be analysed 3.3 is thus illuminated by an incident beam 3.8, the polarisation states of which may be modified, because of the residual birefringencies of the optical fibre 3.10, with respect to the beam generated by the light source 3.4. These residual birefringencies do not however modify the orthogonal character of the polarisation states of the light beam.

The receiving device 3.2 is adapted to receive the resultant light beam 3.9 coming from the object to be analysed 3.3, following the illumination thereof by the light beam 3.8. The receiving device 3.2 preferably comprises a photodiode 3.5, the bandwidth of which is suitable for measuring an optical signal at the frequency $\Delta v$. The photodiode 3.5 is connected to the optical fibre 3.10 via which the light beam 3.9 is received and transported. In the same way as before, the residual birefringencies of the optical fibre 3.10 do not modify the orthogonal, or non-orthogonal, character of the polarisation states of the resultant light beam 3.9.

A fibre-type circulator 3.11 with three channels may be placed in the optical fibre 3.10; the first channel is then connected to the fibre part on the same side as the transmitting device 3.1, the second channel to the fibre part on the same side as the object to be analysed 3.3 and the third channel to the part of the fibre on the same side as the receiving device 3.2. A fibre-type coupler can be used in replacement for the fibre-type circulator.

In order to dispense with the circulator or coupler, two adjacent fibres may be used. The first one is connected to the transmitting device and illuminates the object to be analysed. The second one is connected to the receiving device and transports the light back-scattered by the object or a part of the object to be analysed.

A fibre with several cores may advantageously be used. One core is connected to the transmitting device and illuminates the object to be analysed. One or more other cores are connected to the receiving device and transport the light back-scattered by the object or a part of the object to be analysed.

As before, the transmitting device 3.1 can be adapted to illuminate only part of the object to be analysed 3.3 and the receiving device 3.2 adapted to receive the light beam back-scattered by this part of the object to be analysed 3.3.

The system shown in FIG. 3 is particularly suitable for performing analyses when the object to be analysed is difficult to access, and is for example a system for endoscopic analysis by polarimetric images.

FIG. 4 schematically illustrates a third embodiment of a system of analysis by determining the depolarising or dichroic character of an object 4.3.

Implementation of the system shown in FIG. 4 is similar to that of the system of FIG. 1, except that an optical fibre 4.11 is used to transfer, with respect to the position of the object to be analysed 4.3, the generation of the incident light beam 4.8 serving to illuminate the object to be analysed 3.3 and that an optical fibre 4.11 is used to transfer, with respect to the position of the object to be analysed 4.3, the analysis of the light beam 4.9 resulting from illumination of the object to be analysed 4.3.

The system comprises transmitting 4.1 and receiving 4.2 devices.

The optical fibre 4.11 or the optical fibre 4.12 may be omitted. In this case, the transmitting device 4.1 is replaced by the transmitting device 1.1, or respectively the receiving device 4.2 is replaced by the receiving device 1.2.

The transmitting device 4.1 comprises a light source 4.4 adapted to generate a light beam consisting of signals with two distinct optical frequencies $v_1$ and $v_2$ and with orthogonal polarisation states. The light source 4.4 is also adapted to illuminate the object to be analysed 4.3 via the optical fibre 4.11. The object to be analysed 4.3 is thus illuminated by an incident beam 4.8, the polarisation states of which may be modified, because of the residual birefringencies of the optical fibre 4.11, with respect to the beam generated by the light source 4.4. These residual birefringencies do not however modify the orthogonal character of the polarisation states of the light beam.

The receiving device 4.2 is adapted to receive the resultant light beam 4.9 coming from the object to be analysed 4.3, following the illumination thereof by the light beam 4.8. The receiving device 4.2 preferably comprises a photodiode 4.5, the bandwidth of which is suitable for measuring an optical signal at the frequency $\Delta v$. The photodiode 4.5 is connected to the optical fibre 4.12 via which the light beam 4.9 is received and transported. In the same way as before, the residual birefringencies of the optical fibre 4.12 do not modify the orthogonal, or non-orthogonal, character of the polarisation states of the resultant light beam 4.9.

As before, the transmitting device 4.1 may be adapted to illuminate only part of the object to be analysed 4.3 and the receiving device 4.2 adapted to receive the light beam transmitted by this part of the object to be analysed 4.3.

The system shown in FIG. 4 is particularly suitable for performing analyses when the environment in which the object to be analysed is installed becomes hostile. For example, said system is a system for analysing mechanical or temperature stresses undergone by the object to be analysed 4.3. The dichroic character of the object to be analysed 4.3 then changes according to the mechanical or temperature stresses applied to the object to be analysed 4.3. The object to be analysed 4.3 may for example in this case be a sensor with syndiotactic polypropylene in order to perform an analysis of mechanical stresses.

Such a system for analysing mechanical or temperature stresses may be implemented on the basis of the system presented in relation to FIG. 3. In this case, a mirror may be placed beyond the object to be analysed 4.3 in order to perform a retro-reflection of the light beam.

The invention claimed is:

1. An analyzing system for performing analysis by determining a depolarizing or dichroic character of all or part of an object to be analyzed, said system comprising a transmitting device and a receiving device, wherein the transmitting device is configured for:
   illuminating the object to be analyzed, or a part of the object to be analyzed, by a first light beam consisting of two distinct optical frequencies with first orthogonal polarization states; wherein the transmitting device has one of the following arrangements:
   a first arrangement in which a light source directly illuminating the object to be analyzed;
   a second arrangement in which a light source transferring the first light beam via a first optical guide that illuminates the object to be analyzed; and
   a third arrangement in which a light source illuminating the object to be analyzed via a light-beam splitter that has no effect on the first light beam;
wherein the receiving device comprises an electrical signal producing device producing an electrical signal, from a second light beam with second polarization states and resulting from the illumination of the object to be analyzed by said first light beam, the electrical signal producing device being insensitive to light polarization, and wherein the receiving device has one of the following arrangements:

the electrical signal producing device receives the second light beam directly from the illuminated object to be analyzed, when the transmitting device has the first arrangement;

the electrical signal producing device receives the second light beam directly via a second optical guide which receives light beam directly from the illuminated object to be analyzed, when the transmitting device has the second arrangement; and the electrical signal producing device receives the second light beam directly via said light-beam splitter which redirects light beam retro-reflected by the illuminated object to be analyzed, when the transmitting device has the third arrangement, and wherein the receiving device comprises a dector configured for detecting, from said electrical signal, a signal at a beat frequency equal to a difference between the two optical frequencies constituting said first light beam, and analyzer configured for obtaining information relating to the depolarizing or dichroic character of the object to be analyzed, or of said part of the element to be analyzed, according to the detection of a signal at the beat frequency.

2. The analyzing system according to claim 1, wherein obtaining the information relating to the depolarizing or dichroic character of the object to be analyzed, or of said part of the object to be analyzed, comprises determining the amplitude of the signal at the beat frequency.

3. The analyzing system according to claim 1, wherein the receiving device is configured for capturing light and for converting a captured light signal into the electrical signal, according to a bandwidth defined according to the beat frequency.

4. The analyzing system according to claim 1, wherein said analyzing system is configured for generating a complete or partial image of the object to be analyzed from information relating to the depolarizing or dichroic character of several parts of the object to be analyzed.

5. A method of performing analysis by determining a depolarizing or dichroic character of all or part of an object to be analyzed, said method being implemented by an analysis system comprising a transmitting device and a receiving device, wherein the transmitting device performs:

illuminating the object to be analyzed, or a part of the object to be analyzed, by a first light beam consisting of two distinct optical frequencies with first orthogonal polarization states; wherein the transmitting device has one of the following arrangements:

a first arrangement in which a light source directly illuminating the object to be analyzed;

a second arrangement in which a light source transferring the first light beam via a first optical guide that illuminates the object to be analyzed; and a third arrangement in which a light source illuminating the object to be analyzed via a light-beam splitter that has no effect on the first light beam;

wherein the receiving device comprises an electrical signal producing device producing an electrical signal, from a second light beam with second polarization states and resulting from the illumination of the object to be analyzed by said first light beam, the electrical signal producing device being insensitive to light polarization, and wherein the receiving device has one of the following arrangements:

the electrical signal producing device receives the second light beam directly from the illuminated object to be analyzed, when the transmitting device has the first arrangement;

the electrical signal producing device receives the second light beam directly via a second optical guide which receives light beam directly from the illuminated object to be analyzed, when the transmitting device has the second arrangement; and the electrical signal producing device receives the second light beam directly via said light-beam splitter which redirects light beam retro-reflected by the illuminated object to be analyzed, when the transmitting device has the third arrangement, and wherein the receiving device performs:

detecting, from said electrical signal, a signal at a beat frequency equal to a difference between the two optical frequencies constituting said first light beam; and obtaining information relating to the depolarizing or dichroic character of the object to be analyzed, or of said part of the object to be analyzed, according to the detection of a signal at the beat frequency.

* * * * *